United States Patent [19]
Graff

[11] Patent Number: 5,760,891
[45] Date of Patent: Jun. 2, 1998

[54] WOUND WEB ROLL SIDEWALL QUALITY MEASUREMENT

[75] Inventor: Ernest A. Graff, Ontario, N.Y.

[73] Assignee: Eastman Kodak Company, Rochester, N.Y.

[21] Appl. No.: 583,353

[22] Filed: Jan. 5, 1996

[51] Int. Cl.⁶ ................................................. G01N 21/00
[52] U.S. Cl. .................... 356/237; 356/237; 356/375; 242/67.3; 242/56; 242/57; 242/57.1
[58] Field of Search ....................... 356/237, 375; 242/67.3, 56, 57, 57.1

[56] References Cited

U.S. PATENT DOCUMENTS

| | | |
|---|---|---|
| 3,086,729 | 4/1963 | Mayhew. |
| 4,485,674 | 12/1984 | Ragle. |
| 4,565,927 | 1/1986 | Ragle. |
| 4,679,744 | 7/1987 | Chikamasa et al.. |
| 5,149,980 | 9/1992 | Ertel et al.. |
| 5,237,404 | 8/1993 | Tanaka et al.. |
| 5,329,358 | 7/1994 | Horijon. |
| 5,339,154 | 8/1994 | Gassler et al.. |
| 5,426,309 | 6/1995 | Davidson et al. ........... 356/237 |
| 5,473,425 | 12/1995 | Tokumaru et al. ........... 356/237 |

Primary Examiner—Frank Gonzalez
Assistant Examiner—Reginald A. Ratliff
Attorney, Agent, or Firm—Susan L. Parulski

[57] ABSTRACT

Method and apparatus for measuring the quality of the planar end surface of a wound roll comprising: optically projecting a line of light onto the planar end surface of the wound roll to generate and reflect an image of the line of light; focusing the reflected image onto an image sensor to obtain a data output; and feeding the data to a processor that measures deviations in the reflected image of the line of light that are caused by variations in the planar end surface of the wound roll.

13 Claims, 6 Drawing Sheets

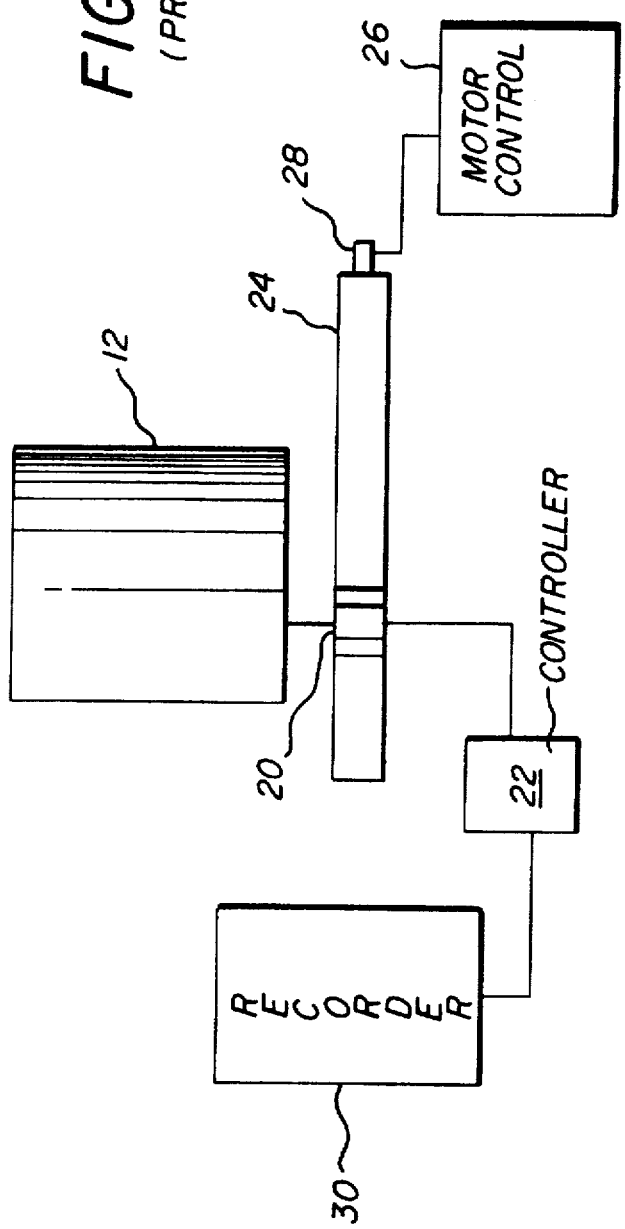
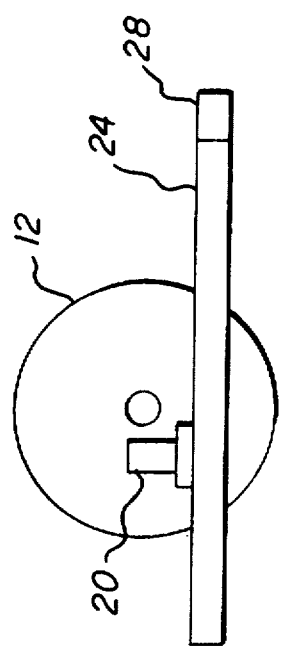
FIG. 2(a) (PRIOR ART)
FIG. 2(b) (PRIOR ART)

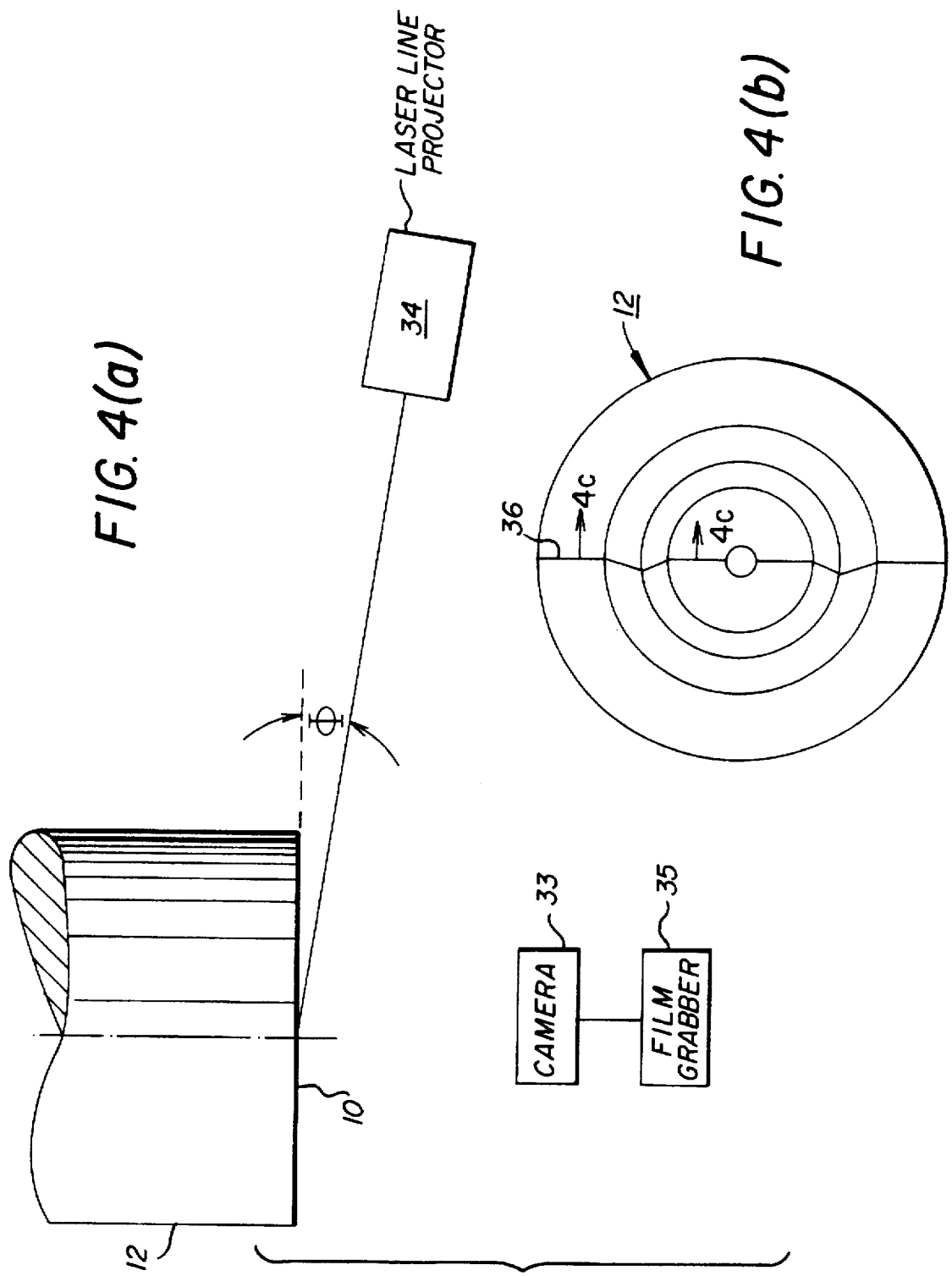

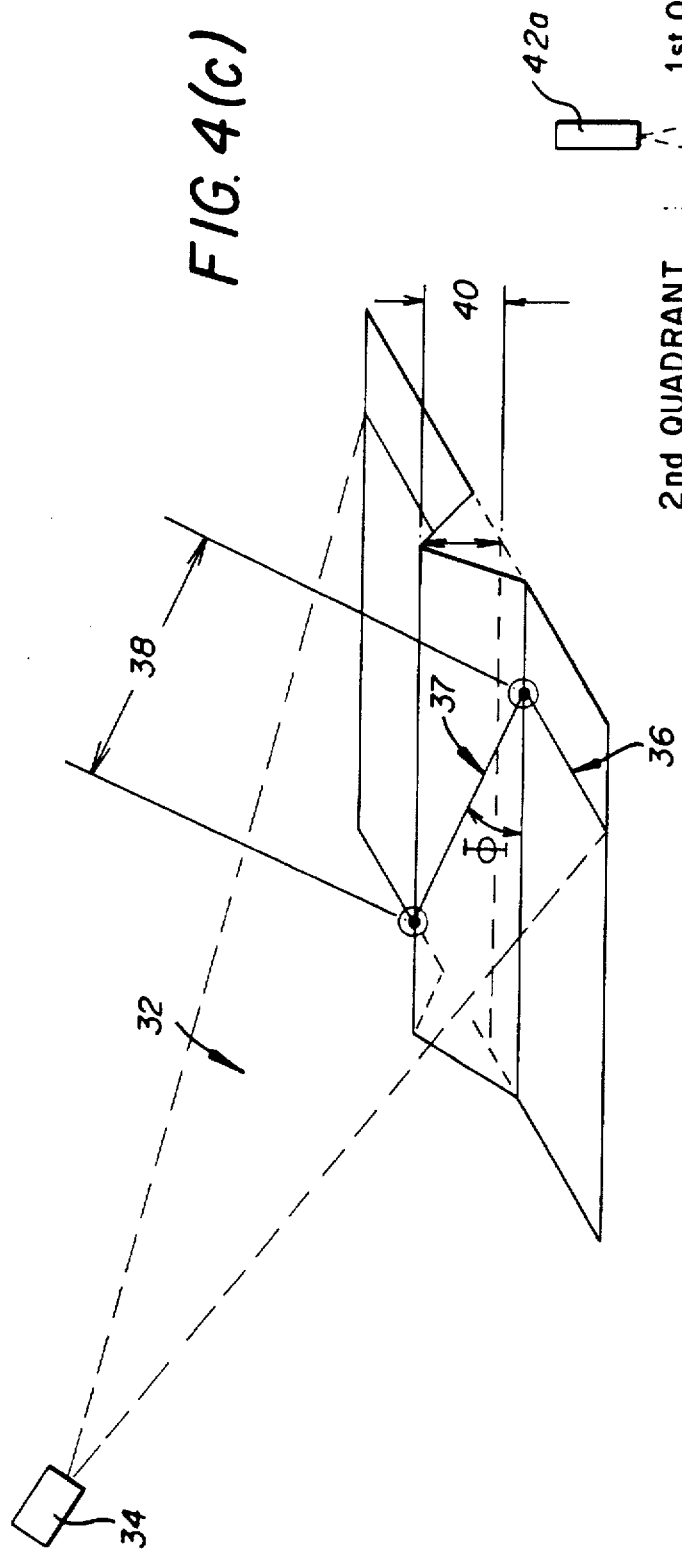
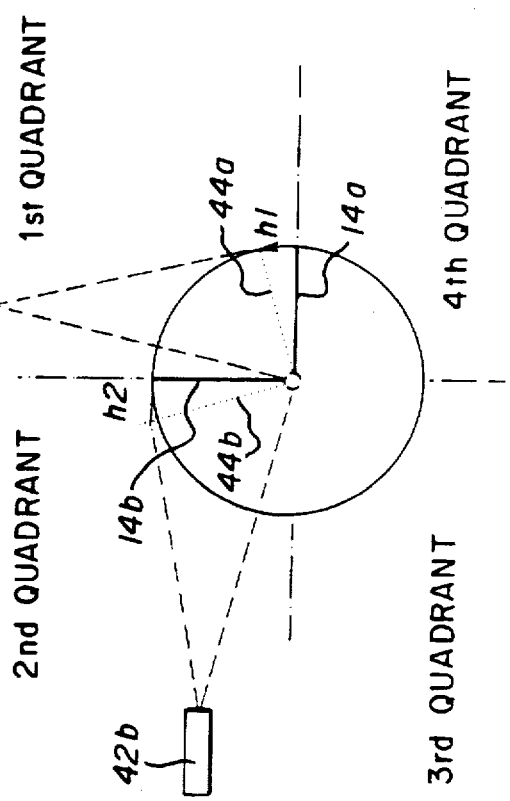
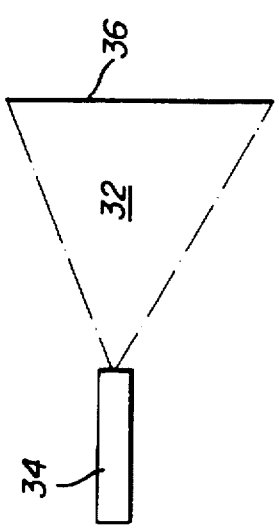

WOUND WEB ROLL SIDEWALL QUALITY MEASUREMENT

FIELD OF THE INVENTION

This invention relates to a method and apparatus for measuring the alignment of the sidewall formed by a continuous web being wound onto a roll. More particularly, this invention relates to a non-contact method and apparatus for measuring the quality of the sidewall of a wound roll of a film or paper used in photography.

BACKGROUND OF THE INVENTION

In the manufacturing process of photographic films and papers it is important that the rolls being formed have smooth circumferential surfaces and straight lateral edges or sidewalls. The physical qualities of the sidewalls are determined by the presence or lack of parameters of dishing, gramophoning, wobble, single lap offset and record placement. These parameters are shown in FIGS. 1(a) through 1(e) and can be defined as follows.

Dishing, illustrated in FIG. 1(a), is the gradual sloping of the sidewall (10) of a roll (12) from a perpendicular line that extends outwardly from the axis (14) of the roll and is on the plane of a core (16).

Gramophoning is shown in FIG 1(b). Gramophoning is a series of hills and valleys on the sidewall (10) of the wound roll (12) that resemble the grooves in a record.

Wobble occurs when the sidewall (10) is not perpendicular to the axis (14) of the roll (12), as shown in FIG. 1(c).

Single Lap Offset, illustrated in FIG. 1(d), occurs when one or more laps (18) of the roll (12) extends outwardly from the sidewall (10).

Record Placement is the alignment of the sidewall (10) of the wound roll (12) to the end of the core (16), as shown in FIG. 1(e).

A typical method for measuring the qualities of the sidewall of a wound roll is shown in FIG. 2. The method comprises: mounting a laser triangulating displacement sensor, such as a Keyenc LB12 Laser Displacement Sensor (20) and Keyenc LB72 controller (22), on a traversing mechanism (24). This traversing mechanism is mounted in such a manner as to allow the displacement sensor (20) to be traversed across the face of the sidewall perpendicular to the axis of the roll. The movement of the sensor is controlled by a motor control (26) and motor (28). As the sensor is traversed across the face of the sidewall, variations in the distance between the sensor (20) and the sidewall are converted to a voltage by the controller (22). This output voltage can be recorded on a strip chart recorder (30) or collected by a computerized data acquisition system for analysis and display. The display is illustrated in FIG. 3. The limitations of this approach are: it is an off-line measurement; the substantial time required to traverse the Keyenc; the high cost of the traversing mechanism; and the difficulty of aligning the traversing mechanism to the roll.

U.S. Pat. No. 4,679,744 discloses a method of measuring the quality of the sidewall of a wound or winding roll of magnetic tape. The sidewall is illuminated from a light source at 45 degrees from the surface of the sidewall, illuminating toward the core of the roll. If there are any single lap offsets or gramophoning, the variations will cast a shadow. These shadows can be viewed with a CCD (Charged Couple Device) camera, thus giving some measure of the quality of the sidewall. The limitations of the method is that if the rate of deviation in the sidewall does not exceed 45 degrees, in the direction of the illumination source and camera, no shadow will be cast and the deviations will not be detected. Also any deviations in the sidewall that are in directions away from the illumination source and camera will not cast a shadow, and thus will not be detected by the method.

SUMMARY OF THE INVENTION

In its broadest aspect, the present invention provides a method for measuring the quality of the planar end surface or sidewall of a wound roll, the method comprising:

optically projecting, at an acute angle, a line of light onto the sidewall of the wound roll to generate and reflect an image of the line of light;

focusing the reflected image onto an image sensor to obtain an output of data; and feeding said data to a processor that measures deviations in the reflected image of the line of light that are caused by variations in the planar end surface of the wound roll.

In its broadest aspect, the present invention provides an apparatus for measuring the quality of the planar end surface or sidewall of a wound roll, said apparatus comprising:

a device to optically projecting, at an acute angel, a line of light onto the sidewall of the wound roll to generate and reflect an image of the line of light;

an image sensor to receive the reflected image; and a processor to receive the reflected image that measures deviations in the reflected image of the line of light that are caused by variations in the planar end surface of the wound roll.

In a further aspect, the present invention provides a non-contact on-line measurement of the quality of the sidewall of a wound roll, such as films and papers used in the imaging industry. The measurement includes dishing, gramophoning, wobble, single lap offset, and record placement, the presence of which deleteriously affect the quality of the wound roll. The method of measurement comprises the steps of:

positioning a laser line projector horizontally with respect to the sidewall of the wound roll;

projecting a laser line by said laser line projector onto the sidewall of the wound roll at an angle of 5–45 degrees, preferably at an angle of about 10 degrees, relative to a plane perpendicular to the axis of the wound roll, and horizontally with respect to the sidewall of the wound roll and through the axis of the roll outwardly toward the edge of the roll;

viewing the projected laser line with a CCD camera;

capturing the viewed laser line and recording data generated thereby using a video processing apparatus; and determining defects in the sidewall by calculating the deviation of the projected line using the angle between the projected line and the perpendicular plane of the sidewall.

It is preferable to use an I/R (infrared) laser for measuring defects in photographically sensitive products in order to prevent interaction between the laser line and the photographically sensitive products.

In its more limited apparatus aspect, the present invention provides an apparatus built from commercially available components, with which non-contact on-line measurement of the quality of the sidewall of a wound roll such as films and papers used in the imaging industry, can be determined.

said quality measurement relating to the presence or absence in the sidewall of a wound roll dishing, gramophoning, wobble, single lap offset and record placement. The apparatus for measuring the quality of the sidewall of a wound roll comprises:

- at least one laser line projector positioned horizontally with respect to the sidewall of the wound roll, said laser line projector projecting a laser line onto the sidewall of the wound roll at an angle of 5-45 degrees, preferably at an angle of about 10 degrees, relative to a plane perpendicular to the axis of the wound roll, and horizontally with respect to the sidewall of the wound roll and through the axis of the roll outwardly toward the edge of the roll;
- at least one CCD camera for continuously viewing the laser line projected onto the sidewall of the wound roll thereby generating data on deviations in the sidewall; and
- at least one frame grabber to record data generated by the CCD camera.

The apparatus may further comprise a computer having a software package to automatically calculate the slope of the projected laser line and the associated deviations in the sidewall of the wound roll.

To detect and measure single lap offset, two laser line projectors and two CCD cameras are used so that both sidewalls of the wound roll will be measured simultaneously.

The details of measurements will be discussed in detail with reference to the drawings.

BRIEF DESCRIPTION OF THE DRAWINGS

The foregoing and other objects, features, and advantages of the invention will be apparent from the following more particular description of the preferred embodiments of the invention, as illustrated in the accompanying drawings.

FIGS. 2(a) and 2(b) represent a typical prior art method for measuring the qualities of the sidewall of a wound roll;

FIG. 4a is a top view of a laser line projector projecting a line on the sidewall of a wound roll;

FIG. 4b is a side view of the wound roll according to FIG. 4a illustrating deviations in the sidewall as they appear as deviations in the projected line;

FIG. 4c is a perspective illustration taken along view 4c-4c of FIG. 4d to illustrate the gain in sensitivity of the method of the present invention;

FIG. 5 is a sketch of a laser line scan projector and projected line;

FIG. 6 is a schematic illustration of the apparatus arrangement for measuring wobble.

DETAILED DESCRIPTION OF THE INVENTION

Figure 1A:
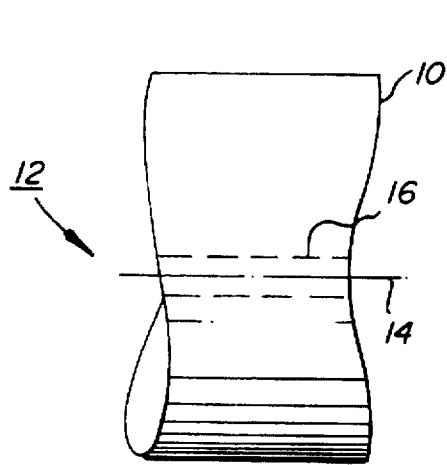
FIGS. 1(a) through 1(e) illustrate the parameters of quality of the sidewall of a roll of film or paper, i.e., dishing, gramophoning, wobble, single lap offset and record placement.
Figure 1B:
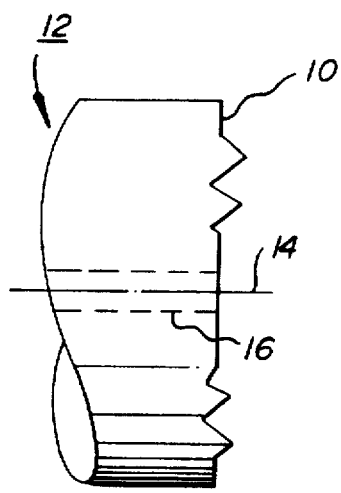
Figure 1C:
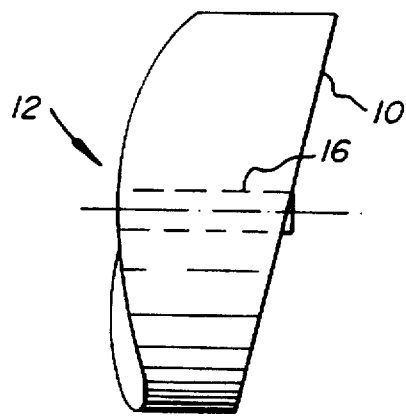
Figure 1D:
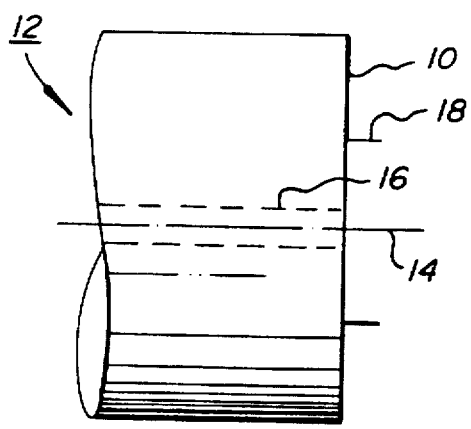
Figure 1E:
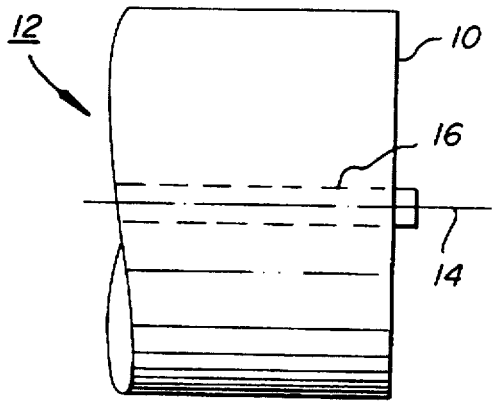
Figure 3:
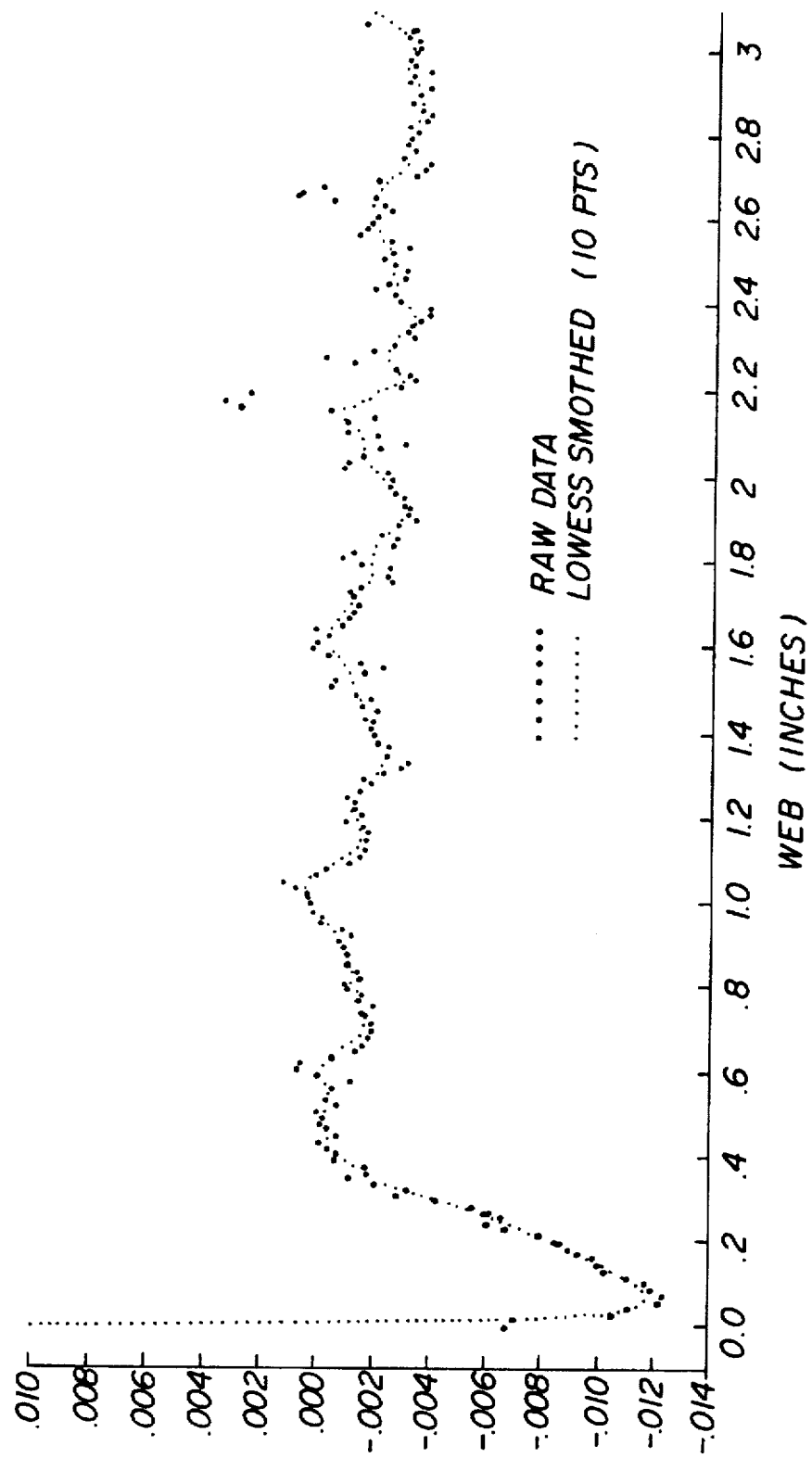
FIG. 3 is a display of the sidewall profile obtained by using a typical prior art apparatus for measuring the qualities of the sidewall.
Figure 7:
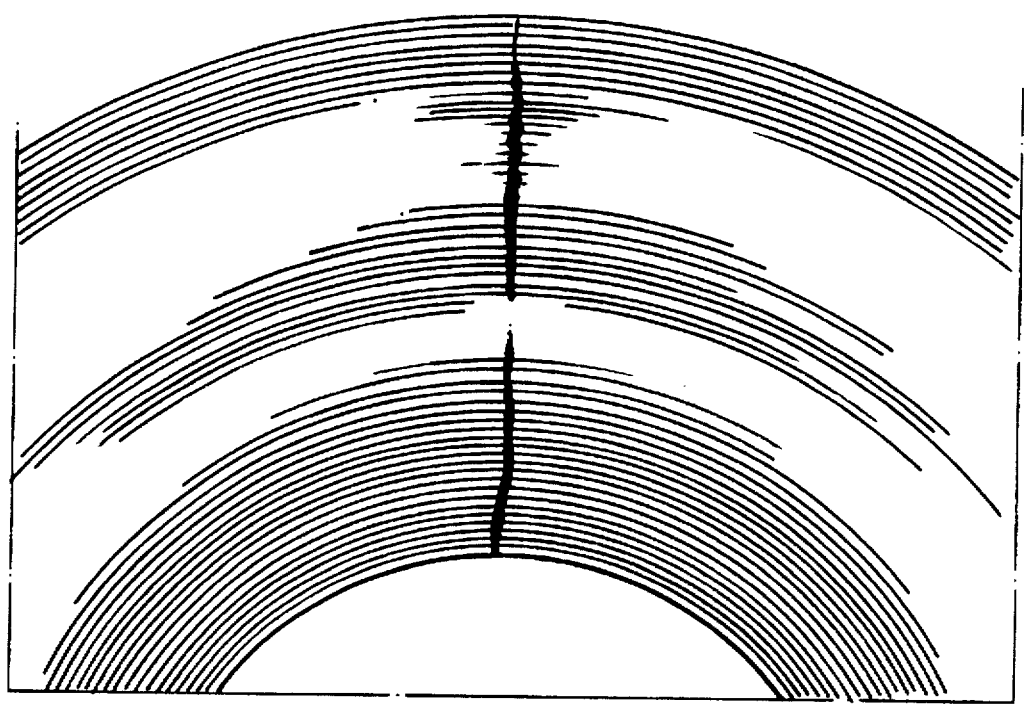
FIG. 7 is a sketch of a projected line on a sidewall showing dishing near the center of the roll and gramophoning near the outer portion of the roll.

The present invention utilizes commercially available parts and components to provide the apparatus with which the objects of the invention may be accomplished.

A laser with a cylindrical lens is available from several manufacturers, such as from Melles Griot and Laser Max. Such a laser with a cylindrical lens is referred to as a laser line projector (34). This lens is able to expand the laser beam in one plane (32), as shown in FIG. 5. Thus, when the laser beam is projected onto a flat surface, it will appear as a straight line (36). If the surface is not flat, the projected line will not be straight. When the laser beam is projected onto the sidewall of a wound roll of paper or film base, any deviations in the sidewall appears as deviations in the laser beam-projected straight line. The deviations are viewed using a CCD camera (33). At least one frame grabber (35) is provided to record the data generated by the CCD camera. The frame grabber inputs as analog video signal from the CCD camera and converts the signal to a digital image. This digital image can then be processed by a computer or a vision processing software. Deviations in the sidewall of a roll are described with reference to FIG. 4.

Referring to FIGS. 4a-4d, a laser line projector (34) projects a vertical line (36) onto the sidewall (10) of the wound roll (12) at an angle phi ($\Phi$). FIG. 4b illustrates how deviations in the sidewall (10) appear as deviations in the projected line (36). An exaggerated view of the deviation in the sidewall (10) is illustrated in FIG. 4c; the deviation is assumed to be symmetrical about the rotational axis for ease of illustration. Laser line projector (34) projects, in a single plane (32), an expanding beam of light onto the sidewall (10) at angle $\Phi$. The features (or defects) (i.e. deviations from a smooth surface and straight line) in the sidewall (10) cause the projected line (36) to be viewed as a deviation (37) from a straight line. If the projected line is viewed at 90 degrees from angle $\Phi$, and angle $\Phi$ is less than 90 degrees, any deviations in the sidewall will result in a viewed deviation (38) in the projected line that is greater than the actual height (40) of the deviation. The viewed deviation (38) is equal to the actual height (40) of the deviation divided by the sine of angle $\Phi$. That is:

Viewed Deviation=Actual Deviation/sin. $\Phi$

From the equation it becomes clear that small deviations in the sidewall can be greatly amplified. For example, at $\Phi=10°$, any deviations in the sidewall would create deviations in the projected line by a factor of approximately 5.76. For large defects a large angle $\Phi$ is sufficient; for small defects, an angle $\Phi$ of between 5°-45° is preferred, most preferably, an angle of 10°.

To detect single lap offsets, two laser line projectors and two CCD cameras are required. The two line scale projectors are installed so that both sidewalls of the wound roll are measured by the same method as above-described with reference to FIG. 4.

Dishing, gramophoning, single lap offset, and record placement are concentric defects around the sidewall of a roll. For this reason, to detect dishing, gramophoning, single lap offset and record placement, a single laser beam line is projected from the axis of the wound roll outwardly on a radius. The laser beam line is viewed by a CCD camera. Viewing the radius of the roll versus the diameter, doubles the sensitivity of the camera and the ability of the apparatus to detect variations in the sidewall. If greater resolution is desired, more than one CCD camera could be used to detect deviations since each of the cameras used would be looking at a smaller area and thereby increasing its ability to detect smaller deviations.

Wobble is encountered with narrow width rolls. To measure wobble, the roll is rotated about its axis while projecting the laser beam line onto the sidewall, and taking measurement with the CCD camera at fixed intervals around the roll. The angular location and maximum wobble is then determined from the measurement.

Another method of measuring wobble is illustrated in FIG. 6. Two laser line projectors (42a and 42b) are installed, preferably at 90° from each other and the laser lines (44a and 44b) are projected onto the sidewall of the roll. Measurements are taken using two CCD camera, not shown in the figure. If the sidewall wobbles in a direction out of page, that is, away from the axis of the roll, the projected line will rotate counter clockwise (CCW) about the axis of the sidewall. Conversely, if the sidewall wobbles in a direction into the page, that is, toward the axis of the roll, the projected line will rotate clockwise (CW). Thus, if the two line projectors placed such that they will project a vertical line and a horizontal line on the sidewall which has a wobble, the projected lines will be reflected into the CCD camera at some location other than the desired vertical (14b) and horizontal (14a) positions. The slope of the projected lines can be calculated using algorithms provided by machine vision software packages which are commercially available. The values of $h_1$ and $h_2$ can then be calculated from the slope of the projected lines; letting deviations in the CCW direction of the projected line from the desired position be defined as positive (+) and the CW deviation defined as negative (−), the magnitude and direction of the maximum wobble can be calculated using the following equation:

$$Max\,Dev = Tan\,(\phi) * \sqrt{h_1^2 + h_2^2}$$

i.e., maximum wobble or maximum deviation is equal to the square root of the sum of $h_1$ squared and $h_2$ squared times Tan $\Phi$. The angle of deviation is Arctan ($h_1/h_2$) and the quadrant (Q) location of the deviation can be found from Table 1.

TABLE 1

| $h_1$ | $h_2$ | Q |
|---|---|---|
| + | + | 1 |
| + | − | 2 |
| − | − | 3 |
| − | + | 4 |

The present invention offers several advantages and conveniences for measuring defects and deviations in the sidewall of rolls including: the measurement can be an on-line measurement during the manufacture of the rolls; cameras and laser line projectors can be positioned at several feet away from the wound roll so that taking measurement does not interfere with the manufacturing operation; the measurement is fast, i.e., the data can be collected in about 1/30 second, the standard camera frame rate, and the processing of data can be accomplished in seconds.

It will also be understood that while the preferred embodiment of the invention has been described, variations may be made thereto without departing from the spirit of the invention.

What is claimed is:

1. A method of measuring the quality of the planer end surface of a wound roll comprising:

optically projecting, at an acute angle less than 45 degrees relative to a plane perpendicular to an axis of the wound roll, a line of light onto the planar end surface of the wound roll to generate and reflect an image of the line of light;

focusing the reflected image onto an image sensor to obtain a data output; and feeding said data to a processor that measures deviations in the reflected image of the line of light from a straight line that are caused by variations in the planar end surface of the wound roll.

2. The method according to claim 1 wherein said line of light is projected by a laser.

3. The method according to claim 2 wherein said laser is an infrared line of light projecting laser.

4. The method according to claim 1 wherein said acute angle is between 5–45 degrees.

5. The method according to claim 1 wherein said acute angle is about 10 degrees.

6. An apparatus for measuring the quality of the planar end surface of a wound roll of light-sensitive media, comprising:

an infra-red laser optically projecting, at an acute angle less than 45 degrees relative to a plane perpendicular to an axis of the wound roll, a line of light onto the planar surface of the wound roll to generate and reflect an image of the line of light;

an image sensor to receive the reflected image; and a processor to receive the reflected image and measure deviations in the reflected image of the line of light from a straight line that are caused by variations in the planar end surface of the wound roll.

7. The apparatus according to claim 6 wherein said acute angle is between 5–45 degrees.

8. The apparatus according to claim 6 wherein said acute angle is about 10 degrees.

9. A non-contact on-line method of measuring the quality of the sidewall of a wound roll of light-sensitive media, comprising the steps of:

positioning an infra-red laser line projector horizontally with respect to the sidewall of the wound roll;

projecting an infra-red laser line by said laser line projector onto said sidewall of the wound roll at an angle of about 5–44 degrees relative to a plane perpendicular to the axis of said wound roll and horizontally with respect to the sidewall of the wound roll and through the axis of the roll outwardly toward the edge of the roll;

viewing the projected laser line with a CCD camera;

capturing the viewed laser line and recording data generated thereby by using a video processing apparatus; and determining defects in the sidewall by calculating the deviation of the projected line from a straight line using the angle between the projected line and the perpendicular plane of the sidewall.

10. The method according to claim 9 wherein said laser line is projected onto said sidewall at an angle of about 10 degrees.

11. An apparatus for measuring the quality of the sidewall of a wound roll of light-sensitive media comprising:

at least one infra-red laser line projector positioned horizontally with respect to the sidewall of the wound roll, said laser line projector projecting an infra-red laser line on the sidewall of the wound roll at an acute angle of about 5–44 degrees relative to a plane perpendicular to the axis of the wound roll, and horizontally with respect to the sidewall of the wound roll, and through the axis of the roll outwardly toward the edge of the roll;

at least one CCD camera for continuously viewing the laser line projected onto the sidewall of the wound roll thereby generating data on deviations of the projected line from a straight line; and at least one frame grabber to record data generated by the CCD camera.

12. The apparatus according to claim 11 further comprising a computer in communication with said CCD camera and having a software package to calculate the slope of the projected laser line and the deviations in the sidewall of the wound roll.

13. The apparatus according to claim 11 wherein said acute angle is about 10 degrees.

* * * * *

UNITED STATES PATENT AND TRADEMARK OFFICE
CERTIFICATE OF CORRECTION

PATENT NO. : 5,760,891
DATED : June 2, 1998
INVENTOR(S) : Ernest A. Graff

It is certified that error appears in the above-indentified patent and that said Letters Patent is hereby corrected as shown below:

On the title page, insert the following item:
-- [60] Provisional application No. 60/002,792 filed Aug. 25,1995.--

Column 1, line 4, insert the following:

--CROSS REFERENCE TO RELATED APPLICATION
Reference is made to and priority claimed from U.S. provisional application Ser. No. 60/002,792, filed Aug. 25, 1995, entitled WOUND WEB ROLL SIDEWALL QUALITY MEASUREMENT.--

Signed and Sealed this

Twenty-fifth Day of August, 1998

Attest:

BRUCE LEHMAN

*Attesting Officer*    *Commissioner of Patents and Trademarks*